(12) United States Patent
Lin et al.

(10) Patent No.: US 10,059,661 B1
(45) Date of Patent: Aug. 28, 2018

(54) METHOD OF FABRICATING [F-18]FEONM PRECURSOR

(71) Applicant: Institute of Nuclear Energy Research, Atomic Energy Council, Executive Yuan, R.O.C., Taoyuan (TW)

(72) Inventors: Shu-Hung Lin, Taichung (TW); Sheng-Po Huang, Taoyuan (TW); Show-Wen Liu, Changhua County (TW); Cheng-Fang Hsu, Taoyuan (TW); Jenn-Tzong Chen, Taipei (TW); Shiou-Shiow Farn, Taoyuan (TW); Wuu-Jyh Lin, Taoyuan (TW); Chyng-Yann Shiue, New Taipei (TW)

(73) Assignee: INTITUTE OF NUCLEAR ENERGY RESEARCH, ATOMIC ENERGY COUNCIL, Executive Yuan, R.O.C., Lungtan, Taoyuan (TW)

( * ) Notice: Subject to any disclaimer, the term of this patent is extended or adjusted under 35 U.S.C. 154(b) by 0 days.

(21) Appl. No.: 15/662,452

(22) Filed: Jul. 28, 2017

(51) Int. Cl.
| | | |
|---|---|---|
| *C07C 303/12* | (2006.01) | |
| *C07C 303/44* | (2006.01) | |
| *C07C 253/34* | (2006.01) | |
| *C07C 253/30* | (2006.01) | |
| *C07C 45/79* | (2006.01) | |
| *C07C 45/65* | (2006.01) | |
| *C07C 221/00* | (2006.01) | |

(52) U.S. Cl.
CPC ............ *C07C 303/12* (2013.01); *C07C 45/65* (2013.01); *C07C 45/79* (2013.01); *C07C 221/00* (2013.01); *C07C 253/30* (2013.01); *C07C 253/34* (2013.01); *C07C 303/44* (2013.01)

(58) Field of Classification Search
CPC ... C07C 303/12; C07C 303/44; C07C 253/34; C07C 253/30; C07C 45/79; C07C 45/65; C07C 221/00
USPC .......................................................... 558/48
See application file for complete search history.

(56) References Cited

U.S. PATENT DOCUMENTS 9,186,423 B1 * 11/2015 Lin .................. A61K 51/04
9,789,207 B1 * 10/2017 Huang ............... A61K 49/0052

FOREIGN PATENT DOCUMENTS

CN        101544584    *  9/2009

OTHER PUBLICATIONS

Machine translation of CN 101544584, 2018.*

* cited by examiner

*Primary Examiner* — Sun Jae Yoo
(74) *Attorney, Agent, or Firm* — Jackson IPG PLLC; Demian K. Jackson

(57) ABSTRACT

A [F-18]FEONM precursor is synthesized. 2-bromoethanol is added to further connect an atom of oxygen at an N terminal of the precursor. Four atoms of carbon can be further connected. Thus, better fat-solubility is obtained along with the increase in carbon. Positioning in brain imaging becomes better.

6 Claims, 1 Drawing Sheet

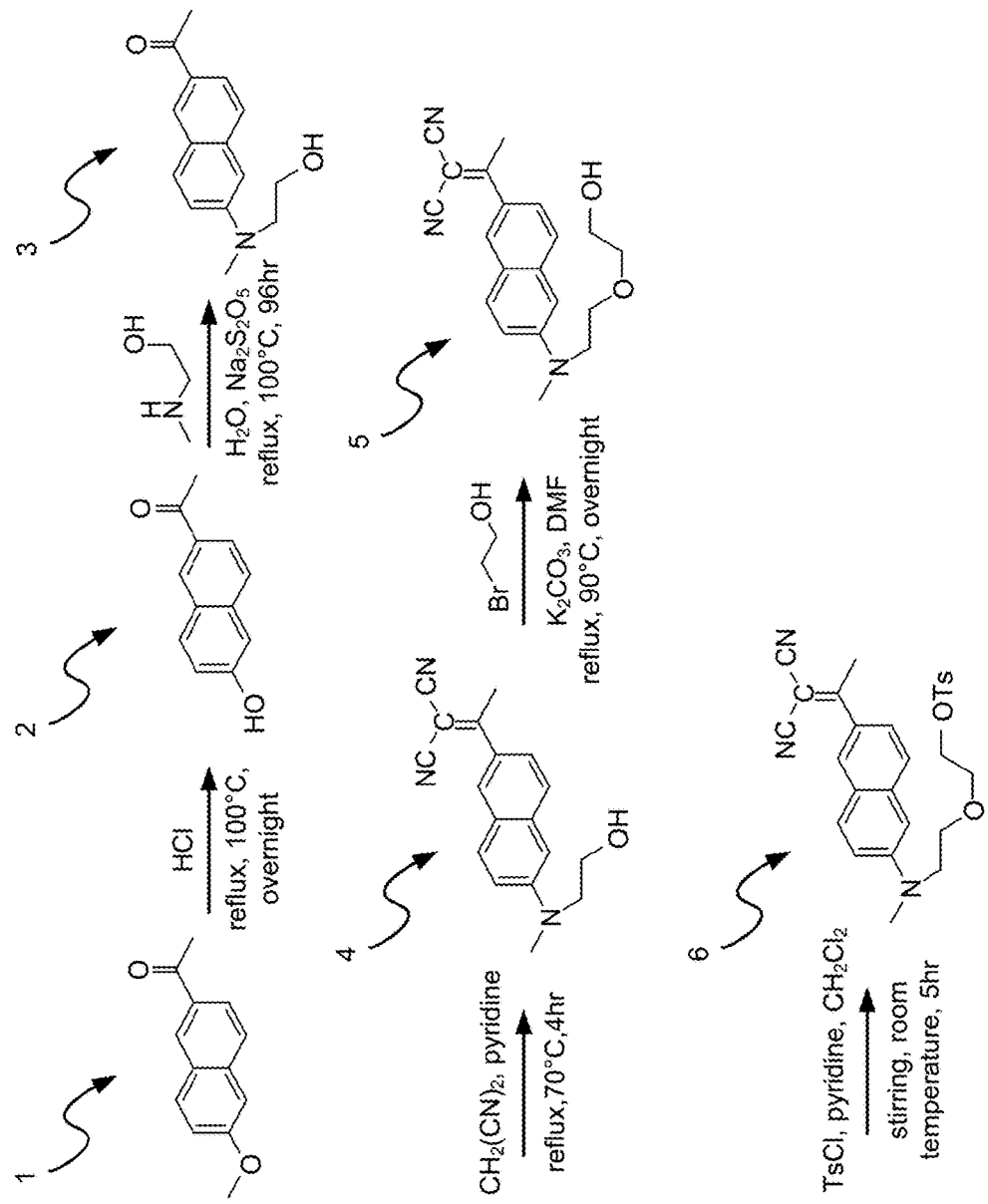

METHOD OF FABRICATING [F-18]FEONM PRECURSOR

TECHNICAL FIELD OF THE INVENTION

The present invention relates to a [F-18]FEONM precursor; more particularly, to fabricating a precursor for brain imaging, where 2-bromoethanol is added for better fat-solubility by carbon increased and positioning in brain imaging becomes better as well.

DESCRIPTION OF THE RELATED ARTS

Alzheimer's disease has become a serious problem on health, society and economy. There are a lot of researches and developments for its early detection and effective treatment.

Positron emission tomography (PET) is a nuclear medical diagnosis technique rapidly developed in recent years. Fluorine-18 (F-18), a radionuclide, is used, which has a relatively long half-life ($t_{1/2}$=110 min) and provides a sufficient time for marking and studying developed image. Its hydrogen-like feature does not cause significant change in the spatial structure and biological activity of molecules. Hence, F-18 is widely used as a radioactive imaging agent in marking glucose, amino acid, fatty acid, nucleoside, receptor-ligand pair, etc. for detecting the functional activity of metabolism, protein synthesis, or neurotransmitter through PET. Thus, diseases and disorders of cancer, heart vascular, neurology and psychiatry are diagnosed for guiding and determining treatment and evaluation. The marking of F-18 and the screening of proper marking agent are the main points for study.

2-$^{18}$F-Fluoro-2-Deoxy-D-glucose ([18F]-FDG) is a widely-used developing agent for PET in the clinical, whose biochemical pathway for metabolism through glucose is used for evaluating the diagnosis and treatment of a variety of brain, cardiac tumors. Yet, it does not completely fulfill the needs of clinical applications. In this regard, through tracking and detection, another study finds radioactive derivatives of Flumazenil is more sensitive and accurate than [18F]-FDG on pointing out the location of disease. Among them, flumazenil difluoro-18 ([18F]-Flumazenil) can be especially used for quantified comparison on the damaged area of brain. It manifests that, for studying molecular changes and developing therapeutic drugs for brain and central-neural-system diseases, [18F]-Flumazenil is a potential tracer worthy of development. However, although many scholars attempt to use F-18 for marking and the image of what is inside an animal is clearly developed, there are still many shortcomings on the marking process. The main shortcoming is that the time for the entire process is too long, including the reaction time. In addition, the product has to be filtered and purified through high performance liquid chromatography (HPLC).

In this regard, a new drug for treating Alzheimer's disease has been found with effects of easy production, saved production time and improved production quantity. But, a commercially applicable method for mass producing the precursor of the drug is not yet available. Hence, the prior arts do not fulfill all users' requests on actual use.

SUMMARY OF THE INVENTION

The main purpose of the present invention is to fabricate a [F-18]FEONM precursor, where 2-bromoethanol is added to further connect an atom of oxygen at N terminal for further connecting four atoms of carbon; and, thus, better fat-solubility is obtained along with the increase in carbon and positioning in brain imaging becomes better as well.

To achieve the above purpose, the present invention is a method of fabricating a [F-18]FEONM precursor, comprising steps of: (a) adding a first compound of 2-acetyl-6-methoxynaphthalene as a starting material in a concentrated hydrochloric acid (HCl) solution to be mixed at an equivalence ratio of 1±20 percents (%):60±20% of the first compound to HCl; heating to reflux overnight to turn solution color from yellow to black; and obtaining a second compound after purification; (b) under an argon condition, adding the second compound, deionized pure water, 2-methylaminoethanol and sodium metabisulfite ($Na_2O_5S_2$) to be mixed at an equivalence ratio of 1±20%:0.08±20% of the second compound to 2-methylaminoethanol; heating to 100 celsius degrees (° C.)±20% with stirring to reflux for 94±20% hours to turn solution color from black to yellow; monitoring reaction through thin layer chromatography (TLC) with a ratio of 1:1 of ethyl acetate (EtOAc) to n-hexane; and obtaining a third compound after purification; (c) under an argon condition, adding the third compound and malononitrile ($CH_2(CN)_2$); implanting anhydrous pyridine to be mixed at an equivalence ratio of 1±20%:4±20% of the third compound to $CH_2(CN)_2$; heating to 70° C.±20% with stirring to reflux for 4±20% hours; monitoring reaction through TLC with a ratio of EtOAc:n-hexane=1:1; and obtaining a fourth compound after purification; (d) under an argon condition, adding the fourth compound, potassium carbonate ($K_2CO_3$), anhydrous dimethylformamide (DMF) and 2-bromoethanol to be mixed at an equivalence ratio of 1±20%:3±20%:3±20% of the fourth compound to $K_2CO_3$ and 2-bromoethanol; heating to 90° C.±20% with stirring to reflux overnight; monitoring reaction through TLC with a ratio of EtOAc:n-hexane=1:1; and obtaining a fifth compound after purification; and (e) under an argon condition, adding the fifth compound, p-toluenesulfonyl chloride (TsCl), anhydrous dichloromethane ($CH_2Cl_2$) and anhydrous pyridine to be mixed at an equivalence ratio of 1±20%:4±20% of the fifth compound to TsCl; stirring under a room temperature for 5±20% hours; monitoring reaction through TLC with a ratio of EtOAc:n-hexane=1:1; and obtaining a precursor of [F-18]FEONM having a chemical structural formula of

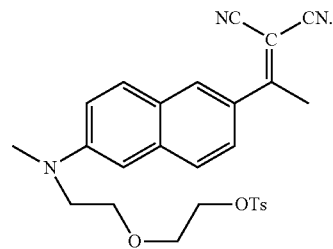

Accordingly, a novel method of fabricating a [F-18]FEONM precursor is obtained.

BRIEF DESCRIPTION OF THE DRAWING

The present invention will be better understood from the following detailed description of the preferred embodiment according to the present invention, taken in conjunction with the accompanying drawing, in which FIG. 1 is the flow view showing the preferred embodiment according to the present invention.

DESCRIPTION OF THE PREFERRED EMBODIMENT

The following description of the preferred embodiment is provided to understand the features and the structures of the present invention.

Please refer to FIG. 1, which is a method of fabricating a [F-18]FEONM precursor, where the [F-18]FEONM precursor has a chemical structural formula as follows:

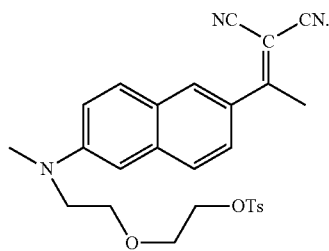 [SMILES: CC(=C(C#N)C#N)c1ccc2cc(N(C)CCOCCOS(=O)(=O)c3ccc(C)cc3)ccc2c1]

The compound having the above formula synthesizes [F-18]FEONM used in developing a contrast agent for positron emission tomography (PET) or, specifically, a nuclear medicine agent for PET on diagnosing Alzheimer's disease (AD) and related diseases or conditions.

The present invention comprises the following steps:

(a) One equivalent of 2-acetyl-6-methoxynaphthalene (referred as a first compound 1 hereinafter) as a starting material is added in sixty equivalents of a 12N hydrochloric acid (HCl) solution to be placed and mixed in a round-bottom flask to obtain a first mixed solution. The first mixed solution is heated with stirring by using magnet to be refluxed overnight until solution color is turned from yellow to black with precipitation. After the first mixed solution is filtered and cooled down, the following steps are processed: dichloromethane ($CH_2Cl_2$) is added for extraction; an aqueous sodium bicarbonate solution and a salt water are used for washing; a layer of organics is collected; dehydration is processed in an organic phase with sodium sulfate; and a second compound 2 is obtained after processing filtration and concentration.

(b) Under an argon condition, a round-bottom flask is added with 1 equivalent of the second compound 2, 0.12 equivalents of deionized pure water, 0.08 equivalents of 2-methylaminoethanol and 0.08 moles (M) of sodium metabisulfite ($Na_2O_5S_2$) to obtain a second mixed solution. The second mixed solution is mixed with stirring by using magnet and heated to 100 celsius degrees (° C.) to be refluxed for 94 hours to turn solution color from black to yellow. The reaction in the flask is monitored through thin layer chromatography (TLC) with a ratio of 1:1 of ethyl acetate (EtOAc) to n-hexane. After the first compound 1 is shown as disappeared in TLC, the following steps are processed: EtOAc is added to process extraction; an aqueous sodium bicarbonate solution and a salt water are used for washing; a layer of organics is collected; and dehydration is processed in an organic phase with sodium sulfate for collecting product through suck-drying. At last, silica-gel column chromatography is processed with a ratio of EtOAc:n-hexane=1:2 as an elution condition to obtain a third compound 3 by collecting final product through suck-drying.

(c) Under an argon condition, a round-bottom flask is added with 1 equivalent of the third compound 3 and malononitrile ($CH_2(CN)_2$) and, then, implanted with 0.6M of anhydrous pyridine to be mixed at an equivalence ratio of 1±20 percents (%):4±20% of the third compound to $CH_2(CN)_2$ to obtain a third mixed solution. The third mixed solution is mixed with stirring by using magnet and heated to 70° C. to be refluxed for 4 hours. The reaction in the flask is monitored through TLC with a ratio of EtOAc:n-hexane=1:1. After the second compound 2 is shown as disappeared in TLC, the following steps are processed: EtOAc is added to process extraction after solvent is suck-dried; an aqueous sodium bicarbonate solution and a salt water are used for washing; a layer of organics is collected; and, dehydration is processed in an organic phase with sodium sulfate for collecting product through suck-drying. At last, silica-gel column chromatography is processed with a ratio of EtOAc:n-hexane=1:1 as an elution condition to obtain a fourth compound 4.

(d) Under an argon condition, a round-bottom flask is added with 1 equivalent of the fourth compound 4, 3 equivalents of potassium carbonate ($K_2CO_3$), 0.3M of anhydrous dimethylformamide (DMF) and 3 equivalents of 2-bromoethanol to obtain a fourth mixed solution. The fourth mixed solution is mixed with stirring by using magnet and heated to 100° C. to be refluxed overnight. The reaction in the flask is monitored through TLC with a ratio of EtOAc:n-hexane=1:1. At last, silica-gel column chromatography is processed with a ratio of EtOAc:n-hexane=1:1 as an elution condition to obtain a fifth compound 5 after purification along with suck-drying.

(e) Under an argon condition, a flask is added with 1 equivalent of the fifth compound 5, 2 equivalents of p-toluenesulfonyl chloride (TsCl), 0.3M of anhydrous dimethylformamide (DMF) and 0.6M of anhydrous pyridine to obtain a fourth mixed solution. The fourth mixed solution is mixed at a room temperature for 5 hours. The reaction in flask is monitored through TLC with a ratio of EtOAc:n-hexane=1:1. At last, silica-gel column chromatography is processed with a ratio of EtOAc:n-hexane=1:1 as an elution condition. After purification along with suck-drying, a sixth compound 6, a precursor of [F-18]FEONM having a chemical structural formula of

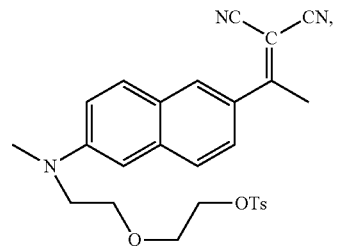 [SMILES: CC(=C(C#N)C#N)c1ccc2cc(N(C)CCOCCOS(=O)(=O)c3ccc(C)cc3)ccc2c1]

is obtained.

Thus, a novel method of fabricating a [F-18]FEONM precursor is obtained.

To sum up, the present invention is a method of fabricating a [F-18]FEONM precursor, where a [F-18]FEONM precursor is fabricated with 2-bromoethanol added to further connect an atom of oxygen at the N terminal for further connecting four atoms of carbon; and, thus, better fat-solubility is obtained along with the increase in carbon and positioning in brain imaging becomes better as well.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of fabricating a [F-18]FEONM precursor, comprising steps of:
   (a) adding a first compound of 2-acetyl-6-methoxynaphthalene as a starting material in a concentrated hydrochloric acid (HCl) solution to be mixed at an equivalence ratio of 1±20 percents (%):60±20% of said first compound to HCl; heating to reflux overnight to turn solution color from yellow to black; and obtaining a second compound after purification;
   (b) under an argon condition, adding said second compound, deionized pure water, 2-methylaminoethanol and sodium metabisulfite ($Na_2O_5S_2$) to be mixed at an equivalence ratio of 1±20%:0.08±20% of said second compound to 2-methylaminoethanol; heating to 100 celsius degrees (° C.)±20% with stirring to reflux for 94±20 hours to turn solution color from black to yellow; monitoring reaction through thin layer chromatography (TLC) with a ratio of 1:1 of ethyl acetate (EtOAc) to n-hexane; and obtaining a third compound after purification;
   (c) under an argon condition, adding said third compound and malononitrile ($CH_2(CN)_2$); implanting anhydrous pyridine to be mixed at an equivalence ratio of 1±20%:4±20% of said third compound to $CH_2(CN)_2$; heating to 70° C.±20% with stirring to reflux for 4±20% hours; monitoring reaction through TLC with a ratio of EtOAc:n-hexane=1:1; and obtaining a fourth compound after purification;
   (d) under an argon condition, adding said fourth compound, potassium carbonate ($K_2CO_3$), anhydrous dimethylformamide (DMF) and 2-bromoethanol to be mixed at an equivalence ratio of 1±20%:3±20%:3±20% of said fourth compound to $K_2CO_3$ and 2-bromoethanol; heating to 90° C.±20% with stirring to reflux overnight; monitoring reaction through TLC with a ratio of EtOAc:n-hexane=1:1; and obtaining a fifth compound after purification;
   (e) under an argon condition, adding said fifth compound, p-toluenesulfonyl chloride (TsCl), anhydrous dichloromethane ($CH_2Cl_2$) and anhydrous pyridine to be mixed at an equivalence ratio of 1±20%:4±20% of said fifth compound to TsCl; stirring under a room temperature for 5±20% hours; monitoring reaction through TLC with a ratio of EtOAc:n-hexane=1:1; and obtaining a precursor of [F-18]FEONM,
   wherein said precursor of [F-18]FEONM has a chemical structural formula as follows:

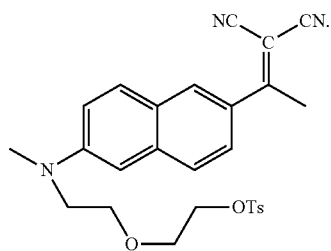 [SMILES: CC(=C(C#N)C#N)c1ccc2cc(N(C)CCOCCOS(=O)(=O)c3ccc(C)cc3)ccc2c1]

2. The method according to claim 1,
   wherein, in step (a), after turning solution color from yellow to black, the following steps are processed:
   (a1) $CH_2Cl_2$ is added to process extraction;
   (a2) an aqueous sodium bicarbonate solution and a salt water are used to process washing;
   (a3) a layer of organics is collected;
   (a4) dehydration is processed with sodium sulfate; and
   (a5) said second compound is obtained after processing filtration and concentration.

3. The method according to claim 1,
   wherein, in step (b), after said first compound is shown as disappeared in TLC, the following steps are processed:
   (b1) EtOAc is added to process extraction;
   (b2) an aqueous sodium bicarbonate solution and a salt water are used for washing;
   (b3) a layer of organics is collected;
   (b4) dehydration is processed with sodium sulfate; and
   (b5) after filtration and concentration, silica-gel column chromatography is processed with a ratio of EtOAc:n-hexane=1:2 and said third compound is obtained.

4. The method according to claim 1,
   wherein, in step (c), after said second compound is shown as disappeared in TLC, the following steps are processed:
   (c1) EtOAc is added to process extraction;
   (c2) an aqueous sodium bicarbonate solution and a salt water are used for washing;
   (c3) a layer of organics is collected;
   (c4) dehydration is processed with sodium sulfate; and
   (c5) after filtration and concentration, silica-gel column chromatography is processed with a ratio of EtOAc:n-hexane=1:1 and said fourth compound is obtained.

5. The method according to claim 1,
   wherein, in step (d), said fifth compound is obtained after purification by using silica-gel column chromatography with a ratio of EtOAc:n-hexane=1:1.

6. The method according to claim 1,
   wherein, in step (e), said precursor of [F-18]FEONM is obtained after purification by using silica-gel column chromatography with a ratio of EtOAc:n-hexane=1:1.

* * * * *